(12) United States Patent
Mante et al.

(10) Patent No.: US 10,954,181 B2
(45) Date of Patent: Mar. 23, 2021

(54) PROCESS FOR SELECTIVELY RECOVERING A PHENOLIC COMPOUND FROM FEEDSTOCK COMPRISING BIO-CRUDE AND/OR BIO-OIL

(71) Applicant: Research Triangle Institute, Research Triangle Park, NC (US)

(72) Inventors: Ofei D. Mante, Research Triangle Park, NC (US); Mustapha Soukri, Research Triangle Park, NC (US); Samuel J. Thompson, Research Triangle Park, NC (US); David C. Dayton, Research Triangle Park, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 16/506,345

(22) Filed: Jul. 9, 2019

(65) Prior Publication Data

US 2020/0017778 A1 Jan. 16, 2020

Related U.S. Application Data

(60) Provisional application No. 62/695,904, filed on Jul. 10, 2018.

(51) Int. Cl.
  *C07C 37/68* (2006.01)
  *C10G 1/00* (2006.01)
  (Continued)

(52) U.S. Cl.
  CPC .......... *C07C 37/685* (2013.01); *C07C 37/004* (2013.01); *C10G 1/002* (2013.01);
  (Continued)

(58) Field of Classification Search
  CPC .................. C10G 1/002; C07C 37/004; C07C 37/68–685
  See application file for complete search history.

(56) References Cited

U.S. PATENT DOCUMENTS

| 2,199,208 A | 4/1940 | Owen et al. |
| 2,301,709 A | 11/1942 | Rumscheidt et al. |
| (Continued) | | |

FOREIGN PATENT DOCUMENTS

| CN | 102899069 | * | 1/2013 | ............. C10G 25/00 |
| CN | 106117006 | * | 11/2016 | ............... C07C 7/04 |

OTHER PUBLICATIONS

Murwanashyaka et al, "Separation of syringol from birch wood-derived vacuum pyrolysis oil", Separation & Purification Technology 24 (2001), pp. 155-165 (Year: 2001).*

(Continued)

*Primary Examiner* — Renee Robinson
(74) *Attorney, Agent, or Firm* — NK Patent Law

(57) ABSTRACT

A process for selectively recovering a phenolic compound from feedstock comprising bio-crude and/or bio-oil is described. The recovery efficiency of the selected phenolic compound is greater than 70 wt % and the purity of the recovered selected phenolic compound is higher than 80 wt %. The process comprises distilling the feedstock to isolate the selected phenolic compound in a first distillate fraction comprising the selected phenolic compound, concentrating the selected phenolic compound from the first distillate fraction in a concentrated mixture, and purifying the concentrated mixture to recover the selected phenolic compound.

18 Claims, 15 Drawing Sheets

(51) Int. Cl.
*C10G 3/00* (2006.01)
*C10G 69/04* (2006.01)
*C07C 37/00* (2006.01)

(52) U.S. Cl.
CPC .............. *C10G 3/50* (2013.01); *C10G 69/04* (2013.01); *C10G 2300/1011* (2013.01); *C10G 2400/30* (2013.01); *Y02P 30/20* (2015.11)

(56) References Cited

U.S. PATENT DOCUMENTS

| | | | |
|---|---|---|---|
| 3,069,354 | A | 12/1962 | Höringklee |
| 4,209,647 | A | 6/1980 | Gallivan et al. |
| 4,233,465 | A | 11/1980 | Gallivan et al. |
| 4,547,596 | A | 10/1985 | Mendiratta et al. |
| 4,827,050 | A | 5/1989 | Peter et al. |
| 4,942,269 | A | 7/1990 | Chum et al. |
| 5,091,499 | A | 2/1992 | Chum et al. |
| 5,223,601 | A | 6/1993 | Chum et al. |
| 5,235,021 | A | 8/1993 | Chum et al. |
| 6,143,856 | A | 11/2000 | Roy et al. |
| 9,944,857 | B2 | 4/2018 | Dayton et al. |
| 2015/0307786 | A1 | 10/2015 | Dayton et al. |
| 2016/0222298 | A1 | 8/2016 | Holle et al. |

OTHER PUBLICATIONS

Li et al, "Production and separation of phenols from biomass-derived bio-petroleum", Journal of Analytical and Applied Pyrolysis 89 (Aug. 2010), pp. 218-224 (Year: 2010).*
Vecino-Mantilla et al, "Methodology for Extraction of Phenolic Compounds of Bio-oil from Agricultural Biomass Wastes", Waste and Biomass Valorization (Jun. 2015), pp. 371-383 (Year: 2015).*
Amen-Chen et al, "Separation of Phenols from Eucalyptus Wood Tar", Biomass and Bioenergy 13 (1997), pp. 25-37 (Year: 1997).*
English Machine translation of CN 102899069 (Year: 2013).*
English Machine translation of CN 106117006 (Year: 2016).*

* cited by examiner

PROCESS FOR SELECTIVELY RECOVERING A PHENOLIC COMPOUND FROM FEEDSTOCK COMPRISING BIO-CRUDE AND/OR BIO-OIL

CROSS-REFERENCE TO RELATED APPLICATION

This application claims the benefit of priority of U.S. Provisional Patent Application No. 62/695,904 titled "PROCESS FOR SELECTIVELY RECOVERING A PHENOLIC COMPOUND FROM FEEDSTOCK COMPRISING BIO-CRUDE AND/OR BIO-OIL", filed Jul. 10, 2018, which is incorporated herein by its entirety by this reference.

STATEMENT REGARDING FEDERALLY SPONSORED RESEARCH OR DEVELOPMENT

This invention was made with government support under Contract No. EE-0007730 awarded by the U.S. Department of Energy, Office of Energy Efficiency and Renewable Energy, Bioenergy Technologies Office. The government has certain rights in the invention.

FIELD

The present disclosure describes an integrated process for selectively recovering a phenolic compound from a bio-oil or bio-crude. The selected phenolic compound may include methoxyphenolic compounds, such as guaiacols or eugenols.

BACKGROUND

A number of industries including pharmaceuticals, natural essential oils, the polymer industry, and the flavor and fragrance industry have a commercial interest in recovering phenolic fractions from feedstock comprising bio-oil and/or bio-crude. Recovering phenolic fractions is more commercially attractive if high purity phenolic fractions can be recovered efficiently with relatively low environmental impact.

Phenolic fractions have been recovered from bio-oils and biocrude using separation techniques such as liquid-liquid extraction (LLE), distillation, and adsorption (e.g., column chromatography) with varying degree of success. Solvent fractionation procedures have also been explored. For example, systematic column chromatographic fractionation of bio-oil with different solvents has been used. With regard to LLE, different protocols/schemes have been used. Most of the LLE methods include a combination of a water-addition step and a base/acid extraction with further solvent separation. The alkaline and organic solvents approach that has extensively been used to recover phenols from petroleum oils has also been demonstrated as a promising method to recover phenolics and neutrals from bio-oils. Furthermore, extraction with switchable hydrophilicity solvents such as tertiary amines (N,N-dimethylcycohexylamine) and supercritical $CO_2$ (Sc—$CO_2$) has been demonstrated as a method for phenolic extraction.

Distillation has also been used for separation of phenolics from bio-oil/bio-crude. Different forms of distillation (steam, molecular, and reactive/extractive distillation) have been explored to overcome the technical challenges associated with conventional distillation of bio-oil. For example, molecular distillation is a typical choice for separation and purification of thermally sensitive materials. Furthermore, adsorption techniques have been used for recovering simple phenols from more dilute streams and for the removal of oxygenated aromatic compounds and other phenolic derivatives from lignin depolymerization streams such as spent liquors.

A disadvantage of many of the reported methods is that the phenolics are isolated from bio-oil/biocrude as one fraction that contains many different kinds of phenolics rather than a more tailored or selective group of phenolics. This drawback is particularly present when solvent extraction and distillation techniques are used. As such, the recovered product contains various kinds of phenols including simple phenols (e.g., phenol, cresol, xylenol, and higher alkylphenols) as well as phenolics with different functionalities like hydroxyl (e.g. catechols), methoxyl (e.g., guaiacols, sygringols, eugenols), carbonyl (e.g., acetovanillone, coniferyl aldehyde, guaiacylacetone, and vanillin), carboxyl (e.g., homovanillic acid), and anisoles. This result is partly because much of the commercial interest has been on recovering phenolic fractions for phenol-formaldehyde resin applications and partly because separation of individual classes of phenols is difficult. Conventional separation methods are not very selective as evidenced in the composition of the phenolic fractions and the fact that several compounds are distributed in different fractions.

Further, depending on the separation method, significant material losses and low recovery efficiency are realized during separation. For instance, alkaline extraction of bio-oil/biocrude results in formation of amorphous residue or tarry caustic soda precipitates. Moreover, some components in the final aqueous phase raffinate are difficult to recover. Other drawbacks with solvent extraction include low throughput and the use of large volumes of solvent and chemicals that require extensive downstream recovery. With regard to distillation as a separation technique, distillation of biocrude is also associated with excessive formation of solid residue (over 50 wt. %) even at lower temperatures (<200° C.). The reduced volatilities and common boiling points of some of the oxygenated components in the bio-oil present a challenge for recovery of chemicals. Further, distillation can be energy intensive. Likewise, adsorptive separations consume large volumes of solvent; adsorbents require regeneration; and multiple-equilibrium-stages can be difficult to attain in a counter-current operation.

Nevertheless, integrating individual separation methods into a hybrid process for recovery of selected phenolics could enable efficient and economical recovery of such phenolics from bio-oil/biocrudes in such a way that overcomes some of the previous challenges. There is a need for processes that address the known challenges with respective to phenolic selectivity, separation efficiency, residual losses, and enhanced purity of the recovered phenolic product as it relates to recovering phenolics from bio-oil/biocrude.

As described herein, separation strategies that integrate distillation, solvent extraction or/and adsorption for the isolation of methoxyphenols from pyrolysis bio-oil/biocrude are disclosed.

SUMMARY OF THE DISCLOSURE

An aspect of the invention includes a process for selectively recovering a phenolic compound from feedstock including bio-crude and/or bio-oil, where the recovery efficiency of the selected phenolic compound is greater than 70 wt % and the purity of the recovered selected phenolic compound is higher than 80 wt %. The process includes: distilling the feedstock to isolate the selected phenolic compound in a first distillate fraction including the selected phenolic compound, concentrating the selected phenolic compound from the first distillate fraction in a concentrated mixture, and purifying the concentrated mixture to recover the selected phenolic compound.

Implementations may include one or more of the following features. The process where concentrating includes using solvent extraction to concentrate the selected phenolic compound in a concentrated mixture. The process where extracting the selected phenolic compound from the first distillate fraction includes adjusting the pH of the first distillate fraction based on the pKa of the selected phenolic compound prior to extraction. The process where solvent extraction is performed at a pH between 9.5 and 13. The process where purifying includes performing adsorption on the concentrated mixture. The process where the selected phenolic compound includes methoxyphenols. The process further including fractionating the feedstock into a volatile fraction and a non-volatile fraction using a solvent prior to distilling and then distilling the volatile fraction.

DETAILED DESCRIPTION

Figure 1:
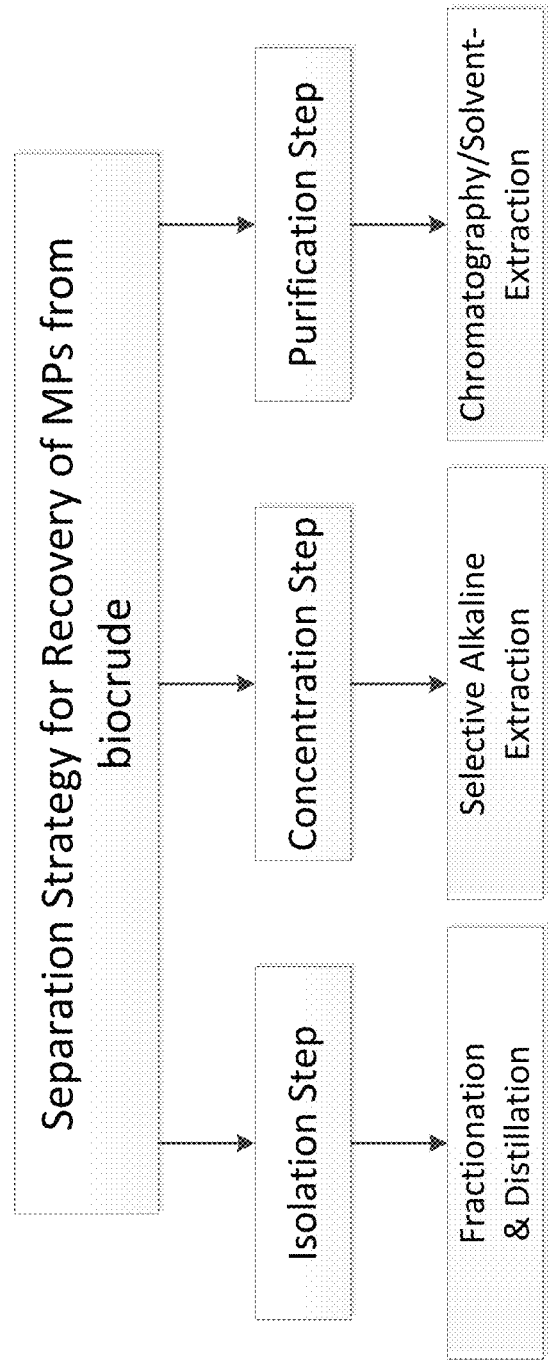
FIG. 1 is a schematic representation in accordance with an embodiment of the integrated recovery method described herein.

Described herein is a method for selectively recovering a phenolic compound from feedstock comprising bio-crude and/or bio-oil. The method comprises distilling the feedstock to isolate the selected phenolic compound in a first distillate fraction comprising the selected phenolic compound, concentrating the selected phenolic compound from the first distillate fraction in a concentrated mixture, and purifying the concentrated mixture to recover the selected phenolic compound. The recovery efficiency is greater than 70 wt % and the purity of the selected phenolic compound is higher than 80 wt %. In embodiments, concentrating comprises using solvent extraction to concentrate the selected phenolic compound in a concentrated mixture. In further embodiments, purifying comprises performing adsorption on the concentrated mixture.

As used herein, the terms "bio-oil" and "bio-crude" can be used interchangeably and are intended to mean the fraction of reaction products obtained from a biomass pyrolysis reaction that is liquid at ambient condition. The liquid-phase products may comprise hydrophilic phase compounds, hydrophobic phase compounds, or a mixture of hydrophilic and hydrophobic phase compounds. The biomass starting material used for pyrolysis can include a wide variety of biological resources. For example, the term biomass can take on the meaning set forth in the Energy Policy Act of 2005. Thus, the term "biomass" can mean: any lignin waste material that is segregated from other waste materials and is determined to be nonhazardous by the Administrator of the Environmental Protection Agency and any solid, nonhazardous, cellulosic material that is derived from—(A) any of the following forest-related resources: mill residues, pre-commercial thinnings, slash, and brush, or nonmerchantable material; (B) solid wood waste materials, including waste pallets, crates, dunnage, manufacturing and construction wood wastes (other than pressure-treated, chemically-treated, or painted wood wastes), and landscape or right-of-way tree trimmings, but not including municipal solid waste (garbage), gas derived from the biodegradation of solid waste, or paper that is commonly recycled; (C) agriculture wastes, including orchard tree crops, vineyard, grain, legumes, sugar, and other crop by-products or residues, and livestock waste nutrients; or (D) a plant that is grown exclusively as a fuel for the production of electricity. Exemplary plants useful as a fuel for energy production include switchgrass, miscanthus, energy canes, sorghum, willows, poplar, and eucalyptus. For example, the biomass starting material for the pyrolysis process may comprise a lignocellulosic material. Exemplary pyrolysis processes are described in commonly owned U.S. Pat. No. 9,944,857, U.S. Patent Application Publication No. 2015/0307786, and U.S. Patent Application Publication No. 2016/0222298, the entire contents of which are incorporated by reference herein.

In embodiments, the described method provides hybrid separation techniques that enable selective recovery of a bio-product constituting phenolic compounds that have a phenolic group, a methoxy group, and substituents such as methyl, ethyl, propyl, and allyl. These phenolic compounds are referred to as monofunctional methoxyphenols (MPs). The phenolic compound may be a guaiacol or a eugenol. The recovered MP bio-product can be used for applications in industries such as flavor & fragrance, pharmaceuticals, natural essential oils, and polymer.

Other phenolic compounds with acidic, ketone, aldehyde, and additional hydroxy functionalities can be recovered as a separate fraction if desired. The described method also can be used to separate syringols and their derivatives from biocrude produced from deciduous woody biomass feedstocks other than conifers. Chemical information for methoxyphenols present in the recovered bioproduct from the biocrude is shown in Table 1. While recovery of MPs is described herein, one of ordinary skill in the art will understand that other phenolic compounds can be recovered using the recovery process described herein.

TABLE 1

Chemical Information of Targeted Methoxyphenols

| Targeted Methoxyphenols | Formula | Structure | Molecular weight (g/mol) | Boiling Point (° C.) | Melting Point (° C.) | pKa |
|---|---|---|---|---|---|---|
| Isoeugenol (cis and trans) | $C_{10}H_{12}O_2$ | 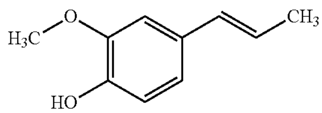 | 164.20 | 267 | −10 | 9.88 |
| Eugenol | $C_{10}H_{12}O_2$ | 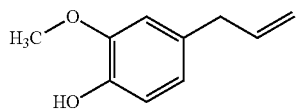 | 164.20 | 253.2 | −7.5 | 10.19 |
| Propylguaiacol (Dihydroeugenol) | $C_{10}H_{14}O_2$ | 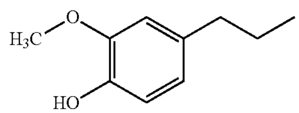 | 166.22 | 240.0 | 16 | 10.29 |
| Ethylguaiacol | $C_9H_{12}O_2$ | 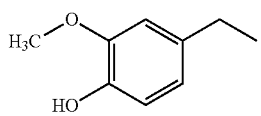 | 152.19 | 228 | 15 | 10.3 |
| Methylguaiacol | $C_8H_{10}O_2$ | 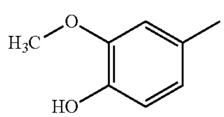 | 138.16 | 221 | 5.5 | 10.27 |
| Guaiacol | $C_7H_8O_2$ | 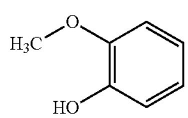 | 124.14 | 205 | 30 | 9.98 |

The selective recovery method may also comprise fractionating the feedstock into a volatile fraction and a non-volatile fraction using a solvent prior to distilling. In this embodiment, the volatile fraction remaining after fractioning can be distilled. Solvent for use in fractionating can be chosen to separate out the desired volatile fraction. For example, the solvent can be non-toxic, have a polarity index less than 3.0, and a water solubility less than 0.5 g/100 mL. In embodiments, the solvent is aromatic and has a boiling point less than 185° C. The solvent may comprise toluene, xylene, ortho-xylene, light cycle oil, and reformate. Fractionating may comprise more than one solvent fractionation step.

The recovery method described herein integrates discrete separation processes to recover phenolic compounds. In particular, the method integrates the processes of isolation, concentration and purification. Various separation techniques can be used for the processes of isolation, concentration and purification. For example, isolation can be achieved by distillation of a mixture of selected phenolic compounds from a feedstock of bio-oil or bio-crude. Concentration of selected phenolic compounds can be can be performed by solvent extraction from a mixture of phenolic compounds; and purification of the concentrated selected phenolic compounds can be accomplished with silica gel adsorption. In embodiments, the integrated recovery method may focus on the isolation of particular methoxyphenolic compounds, such as eugenols and guaiacols. The integrated method enables isolation of particular compounds from feedstock containing bio-oils and bio-crudes without rendering the remaining portion of the feedstock untenable for downstream use (for example, refining into biofuel intermediates).

Advantageously, the hybrid recovery method can reduce or eliminate some of the disadvantages associated with using a single processing technique for recovery of phenolic compounds. For example, the formation of solid residue that can be experienced with distillation can be reduced or eliminated. Moreover, the formation of caustic soda precipitates during alkaline extraction also can be reduced or eliminated. Using adsorption as a final processing step for purification can also reduce solvent requirements, the number of stages, and the rate of media exhaustion.

Integrating processing methods in the hybrid recovery method enables separation efficiencies greater than about 60 wt % and methoxyphenol product purity higher than 80 wt %. For example, the separation efficiency can be between about 60 wt % and about 90 wt %. The separation efficiency can be greater than about 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, or 90 wt %. In embodiments, the purity of the recovered selected phenolic compound can be between about 70 wt % and about 100 wt %. For example, the purity can be higher than about 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt %, 94 wt %, 95 wt %, 96 wt %, 97 wt %, 98 wt %, or 99 wt %.

The recovery method described herein differs from recovery methods involving single processing techniques, which focus on recovering phenolic compounds collectively as a fraction. Rather, the hybrid recovery method enables efficient isolation and selective concentration of methoxyphenols while minimizing significant material losses, for example, as residue during distillation and as a tarry sludge precipitate in alkaline extraction. The recovery method comprises the processing steps of isolation, concentration, and purification. The method may include a neutralization step between the concentration step and the purification step. A neutralization step can be used to free any phenolates prior to purification.

FIG. 1 is a schematic representation of an embodiment of the integrated recovery method summarizing the processing steps.

Isolation

The isolation step comprises distillation. It may also comprise fractionation. If the isolation step includes both distillation and fractionation, fractionation is performed first. A suitable solvent with low water solubility (for example, toluene) can be mixed with the bio-crude feedstock for fractionation. The solvent extracts the volatile component of the bio-crude, and the volatile fraction can be fractionally distilled to obtain a crude MP distillate. Thus, choice of solvent impacts which components are present in the volatile fraction and which components are present in the non-volatile fraction. Fractionation can be performed in such a way that residue forming components such as complex phenolics, anhydrosugars, oligomers, pyrolytic lignin, aromatic acids, and water-soluble compounds such as carboxylic acids, ketones, and aldehydes are not extracted by the solvent.

Preferred solvents have poor solubility for residue forming components present in the feedstock, do not form emulsions when mixed with the bio-oil in the feedstock, and require short residence times to phase separate. In general, solvents with low polarity and low water solubility are suitable solvents. Solvents with a polarity index greater than 3.2 and water solubility more than 7.0 g/100 mL tend to form an emulsion with bio-crude. Thus, solvents with a polarity index less than 3.0 and water solubility less than 0.5 g/100 mL are suitable. Solvents with a polarity index greater than 2.0 and less than 3.2; and water solubility between 0.01 g/100 mL and 0.5 g/100 mL are preferred. Solvents with boiling points less than 185° C. can be used to extract out a fraction that contains neutrals, volatile phenolics, and other less reactive components. Exemplary suitable solvents have boiling points between 35° C. and 185° C. Moreover, suitable solvents can include aromatic fraction solvents such as toluene, naptha, xylene, chlorobenzene, dichlorobenzene and refinery intermediates, such as reformate and light cycle oil (LCO).

In an exemplary embodiment, toluene can be used as a solvent for the fractionation portion of the isolation step. First, the bio-oil/bio-crude can be mixed with toluene in an oil:solvent ratio of 1:0.5 to 1:1 by volume. Upon settling, the volatile fraction, which is a toluene-extract fraction, separates out. The toluene-extract fraction can be distilled to recover the toluene solvent and a crude mixture of MPs.

The fractionation step can include more than one extraction. Performing more than one extraction during the fractionation step may increase the amount of and purity of recovered bio-product. As an example, 500 mL of bio-crude was mixed with 350 mL of toluene for a first extraction. The raffinate from the first extraction was then mixed with 150 mL of toluene for a second extraction. The extracts from both washes can be combined and distilled to recover the toluene solvent and an MP-rich fraction.

Depending on the physicochemical properties of the bio-crude to be separated, multiple extraction steps may be helpful in achieving higher recovery efficiencies. Recovery efficiencies between 80 wt % and 95% are achievable. In testing, guaiacols were generally found to have lower recoveries compared to eugenols. However, multi-stage washes could be employed to enhance the recovery of the guaiacols. In testing, fractionation followed by distillation reduced or eliminated solid residue formation. Rather, a heavy gummy fraction that was able to flow at temperatures of about 40° C. remained after distillation.

The isolation step includes distillation. The distillation temperature can be adjusted depending on the selected phenolic compound bio-product. For example, distillation can be performed to obtain crude MP distillate boiling between 165° C. and 320° C. The operation can be performed in a single or multiple packed distillation columns, in a batch or continuous mode, and at atmospheric pressure or under vacuum. Preferred vacuum conditions are between 1 and 20 kPa. In an exemplary embodiment, a narrow boiling point range (about 195° C.-275° C.) can be used to recover a fraction with a higher concentration of MPs.

Alternatively, the isolation step may comprise co-distillation of all of the bio-oil feedstock with a high-boiling point liquid that can solubilize the bio-oil. An exemplary high-boiling point liquid is glycerol. Glycerol is a by-product from the biodiesel industry that has relatively high solvation for bio-oil and a boiling point (290° C.) that is higher than the boiling range of the targeted methoxyphenols. Triethylene glycol is an additional exemplary high-boiling point liquid that could be used for co-distillation.

Concentration

The concentration step may comprise solvent extraction. A selective alkaline extraction process can be used to concentrate the crude MP-distillate produced during the isolation step. Differences between the acid strength of the phenolic compounds present in the crude distillate can be used to selectively separate out different classes of phenolic compounds with solvent extraction. In fact, even slight differences in acid strength enable selective separation.

The acid dissociation constant for an acid ($K_a$) is a quantitative measure of the strength of the acid in solution. The logarithmic acid dissociation constant (pKa) also can be used as an indicator of acid strength. In general, phenolics are weak Lewis acids and their pKa values are less than 12 in water. Table 2 provides pKa values of some of the phenolic compounds found in the crude MP distillate recovered from loblolly pine biocrude. As can be seen, the pKa of these exemplary phenolic compounds is generally between about 9 and about 11.

TABLE 2

| pKa of exemplary phenolic compounds present biocrude | |
|---|---|
| Selected Phenolics | pKa at 25° C. (in water) |
| 2,4,6-trimethylphenol | 10.88 |
| 2,6-dimethylphenol | 10.66 |
| 5-methyl-2-(propan-2-yl) phenol | 10.62 |
| 2,4-dimethylpneol | 10.6 |
| 2-allyl-4-methylphenol | 10.59 |
| 2,4,5-trimethylphenol | 10.57 |
| 2,3-dimethylphenol | 10.42 |

TABLE 2-continued pKa of exemplary phenolic compounds present biocrude

| Selected Phenolics | pKa at 25° C. (in water) |
|---|---|
| 3,5-dimethylphenol | 10.38 |
| Ethylguaiacol | 10.3 |
| Propylguaiacol (Dihydroeugenol) | 10.29 |
| 2-methylphenol | 10.287 |
| Methylguaiacol | 10.27 |
| 2-ethylphenol | 10.27 |
| 4-methylphenol | 10.26 |
| Eugenol | 10.19 |
| Hydroxyacetophenone | 10.16 |
| Phenol | 10 |
| 4-ethylphenol | 10 |
| Guaiacol | 9.98 |
| 4-propylphenol | 9.98 |
| Benzenediol (catechol) | 9.96 |
| 4-methylcatechol | 9.91 |
| 3-ethylphenol | 9.9 |
| Isoeugenol (cis and trans) | 9.88 |
| Guaiacylacetone | 9.88 |
| Pyrocatechol | 9.66 |
| Coniferyl aldehyde | 9.52 |
| Acetovanillone | 8.17 |
| Vanillin | 7.4 |
| Homovanillic acid | 4.36 |

As also shown, some of methoxyphenols have pKa values between about 9.8 and 10.3. For example, the following methoxyphenols have pKa values in the above-referenced range in the following order: ethylguaiacol>dihydroeugenol>methylguaiacol>eugenol>guaiacol>isoeugenol. Theoretically, the phenolics with higher pKa are weaker acids and vice versa. Given the differences in pKa between methoxyphenolic compounds and other phenolic compounds, alkaline extraction can be used to selectively isolate the MPs from other classes of phenolics. Various bases or acids can be added to the distillate from the isolation step to adjust the pH thereby enabling selective concentration of the desired methoxyphenol compounds. As one of skill in the art understands, pH is related to pKa and can be adjusted as needed.

Most of the methoxyphenols present in bio-crudes can be recovered at a pH between 12.5 and 10. At this pH range, most of the targeted MPs can be selectively separated from other phenolics with lower pKa values, such as benzendiols, guaiacylacetone, pyrocatechol, coniferyl aldehyde, vanillin, acetovanilone, and homovanillic acid. In a preferred embodiment, concentration of the MPs is done between pH 10.5 and 11.5 to separate them from other multifunctional phenolics.

The recovery efficiency and concentration of the MPs are also influenced by the type of solvents used. At pH 10 and above, most phenolics are expected to be in their deprotonated form thereby limiting their extraction by organic solvents. While not being bound by theory, it is surmised that complete protonation of the phenolates is not achieved with the extraction conditions described herein. Rather, it is believed that the addition of the solvent to the aqueous phase establishes equilibrium between the phenolates and the free phenolics and as result, the phenolates can be extracted. Accordingly, organic solvents are useful in extracting both free phenolics and phenolates efficiently. Exemplary solvents include dichloromethane, methyl isobutyl ketone (MIBK), hexane and methyl tertiary butyl ether (MTBE).

Purification

The purification step may comprise adsorption. In embodiments, silica gel adsorption, more particularly, silica gel adsorption in a chromatographic column can be used. Using adsorption as the last step for purification reduces solvent requirements, the number of stages needed for purification, and the rate of media exhaustion.

The integrated recovery method comprises processing techniques to achieve isolation, concentration, and purification. The individual techniques that are used for isolation, concentration, and purification can be selected depending on end use requirements for the recovered bio-product. For example, different industries require different purity standards. Thus, purity standards may be stricter or more lenient depending on the end use of the recovered bio-product.

Three exemplary integrated recovery methods are described below—each using different processing techniques to recover selected phenolic compounds.

Figure 2:
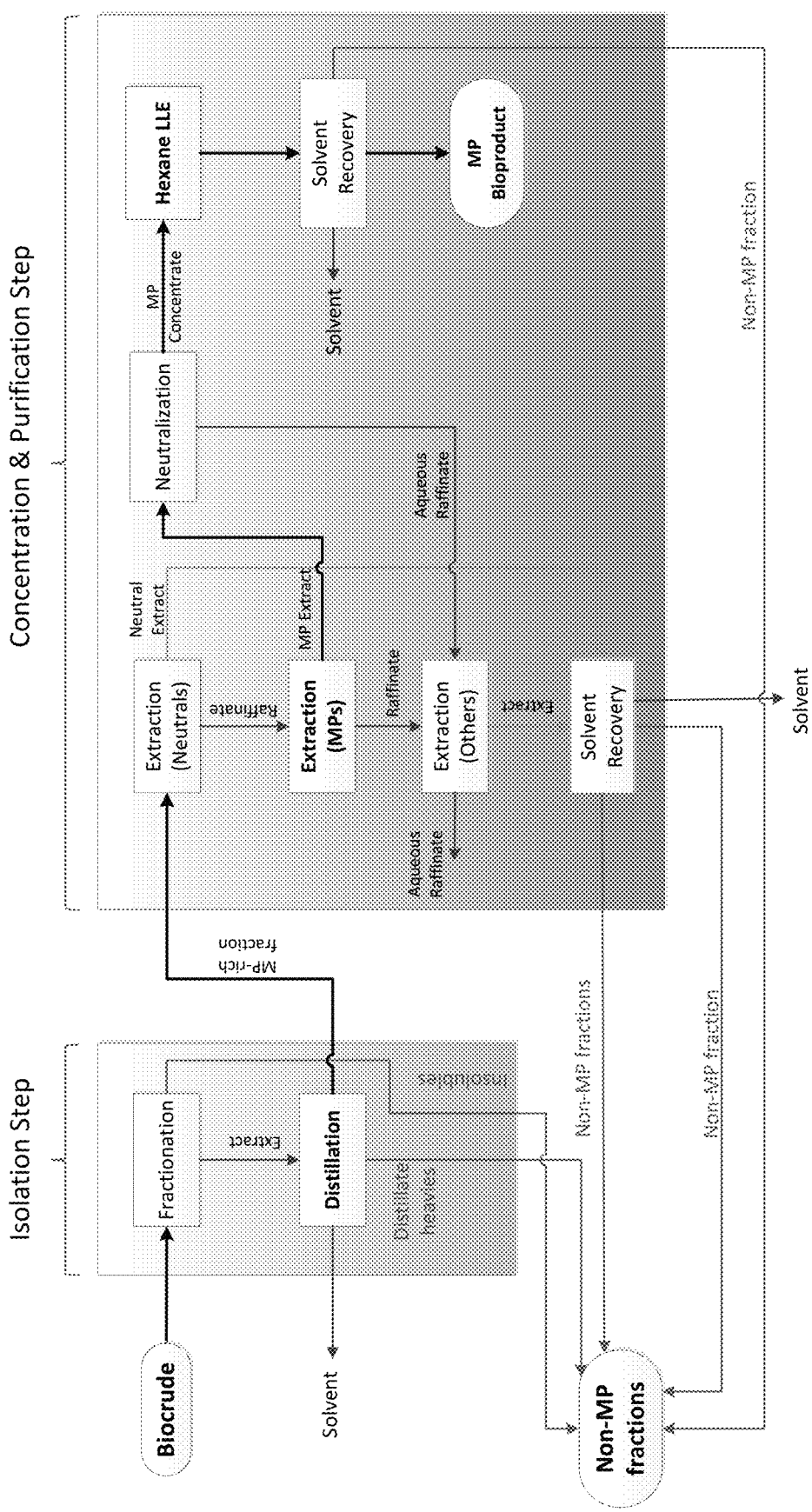
FIG. 2 is a schematic flow diagram of a first exemplary strategy (strategy 1) of an embodiment of the integrated recovery method.
Figure 3:
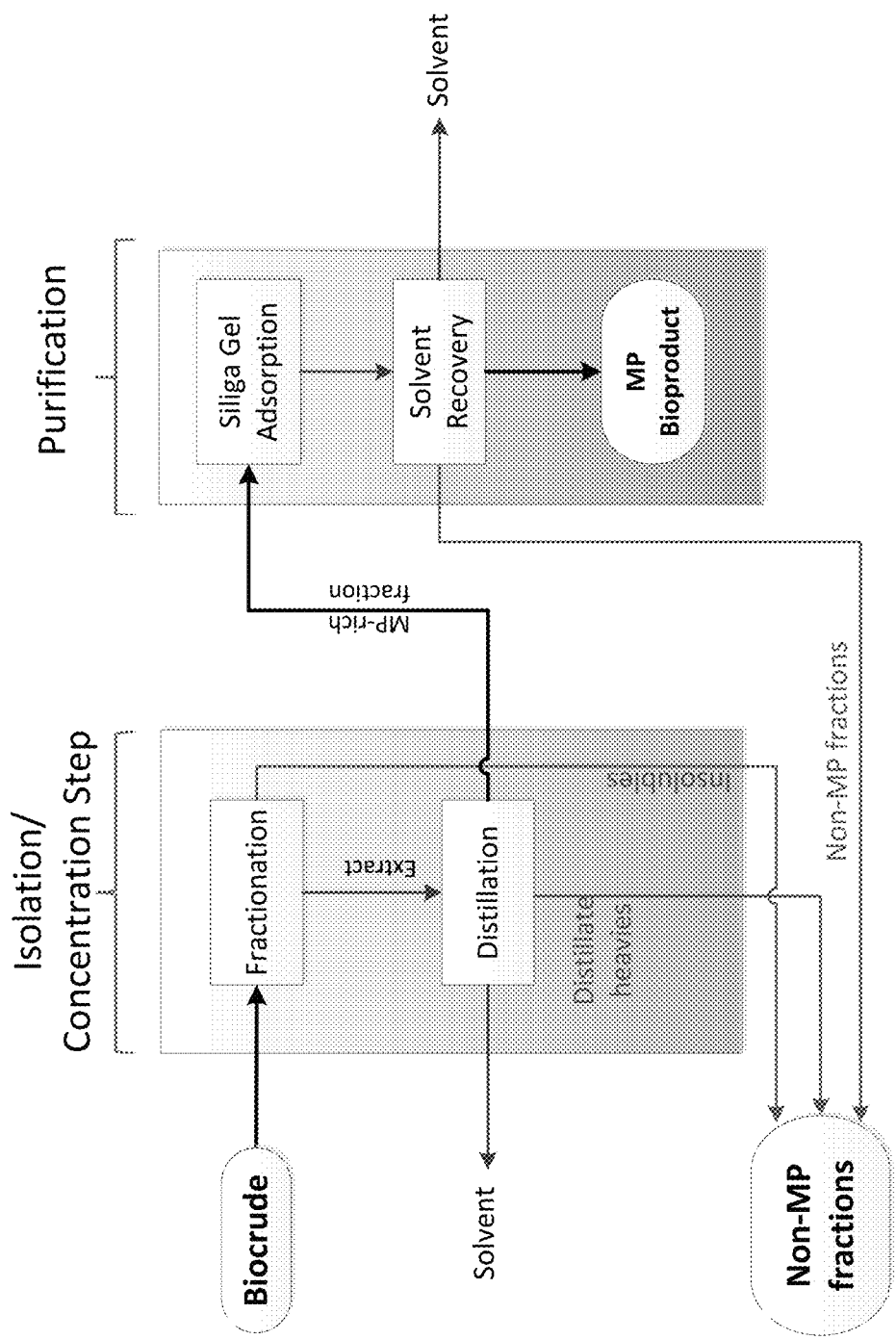
FIG. 3 is a schematic flow diagram of a second exemplary strategy (strategy 2) of an embodiment of the integrated recovery method.
Figure 4:
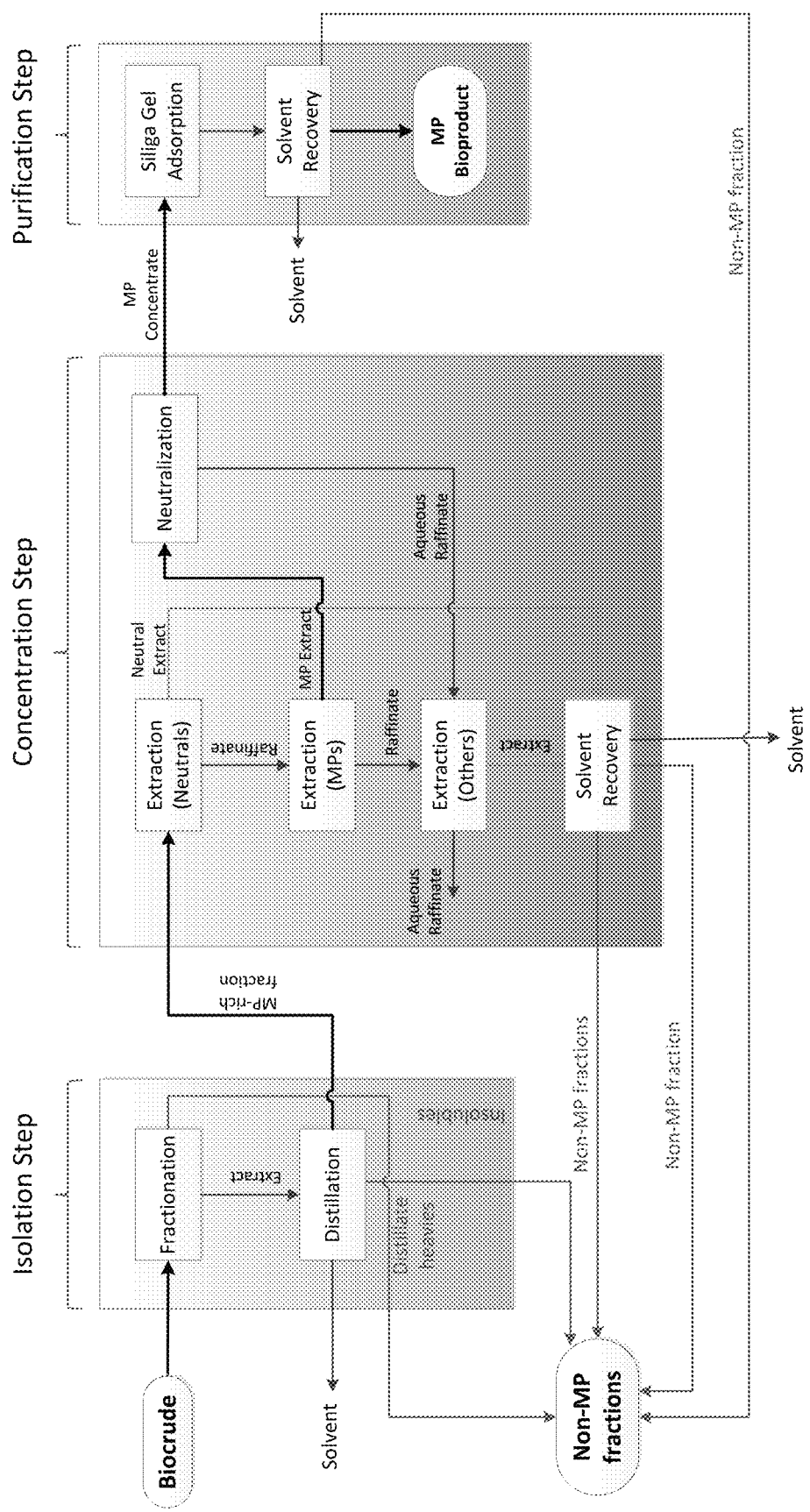
FIG. 4 is a schematic flow diagram of a third exemplary strategy (strategy 3) of an embodiment of the integrated recovery method.

FIG. 2 provides a schematic flow diagram of the first exemplary strategy (strategy 1), which comprises isolation of a crude mixture of MPs by distillation and concentration of the MPs by alkaline extraction with subsequent hexane extraction. FIG. 3 provides a schematic flow diagram of the second exemplary strategy (strategy 2), which integrates fractionation and distillation for isolation and concentration of a mixture of MPs and adsorption for purification of the enriched MPs mixture. FIG. 4 provides a schematic flow diagram of the third exemplary strategy (strategy 3), which comprises fractionation, distillation, solvent extraction, and adsorption for isolation of a crude mixture of MPs; concentration of the MPs; and purification of the concentrated MPs mixture respectively.

All three strategies include isolation, concentration, and purification. Strategies 1, 2, and 3 include fractionation and distillation in the isolation step.

Strategies 1 and 3 include extraction in the concentration step. First, a selective alkaline extraction is used to selectively concentrate the MPs based on their acid strength and the acid strength of other components present in the crude MP distillate. For alkaline extraction, a strong alkaline aqueous solution can be added to the MP distillate fraction to increase the pH thereof to a level where neutral compounds such as ketones, aromatics, and possibly some simple phenols with higher pKa value (>10.35) can be extracted with a hydrophobic-polar solvent such as methyl tertiary-butyl ether (MTBE). The pH of the raffinate can then be reduced with a mineral acid to a level where the targeted methoxyphenols (9.8<pKa<10.3) can be extracted with an organic solvent, as a mixture comprising neutral and basic MPs. The pH of the remaining aqueous solution can be lowered to a level where the remaining components with lower pKa values (<9.8) such as multifunctional phenolics and organic acids can be recovered with the organic solvent. The enriched MPs extract can then be neutralized to free any phenolates prior to purification. Strategy 2 does not include an extraction step for concentration. Rather, strategy 2 uses fractionation and distillation for both the isolation and concentration steps.

Strategy 1 includes hexane extraction as a purification step following the neutralization step. Strategy 2 and strategy 3 include an adsorption bed of silica gel with eluents of hexane-DCM-methanol for purification.

The integrated recovery method enables recovery of selected bio-products with high concentrations and high purities. For example, high concentration and high purity eugenols and guaiacols can be obtained with the described method. Moreover, individual fractions other than the selected phenolic compounds (for example, non-MP fractions) collected at each processing step can be reconstituted for further use (for example, upgrading into fuel products) and/or processed further for the recovery of other chemicals of interest.

EXAMPLES

Example 1

Solvent extraction was performed as an exemplary separation technique for the concentration step. An MP-rich fraction (198 g) with 24 wt % concentration of methoxyphenols was sequentially extracted at the following pH levels: 14.45, 12.51, 6.41, and 1.01. A 50 wt % NaOH solution was added to the MP-fraction to achieve a pH of 14.45. The MP-fraction was cooled in an ice bath while the NaOH solution was being added. MTBE solvent was used to extract the neutral component. A 6N HCl solution was then used to lower the pH of the raffinate from 14.45 to the respective pH levels of 12.51, 6.41, and 1.01. Three washes were performed at each pH level with about 100 mL of MTBE. The volume ratio of the raffinates to the organic solvent was 1:0.5. After extraction, about 23.3 g remained in the last raffinate.

Figure 5:
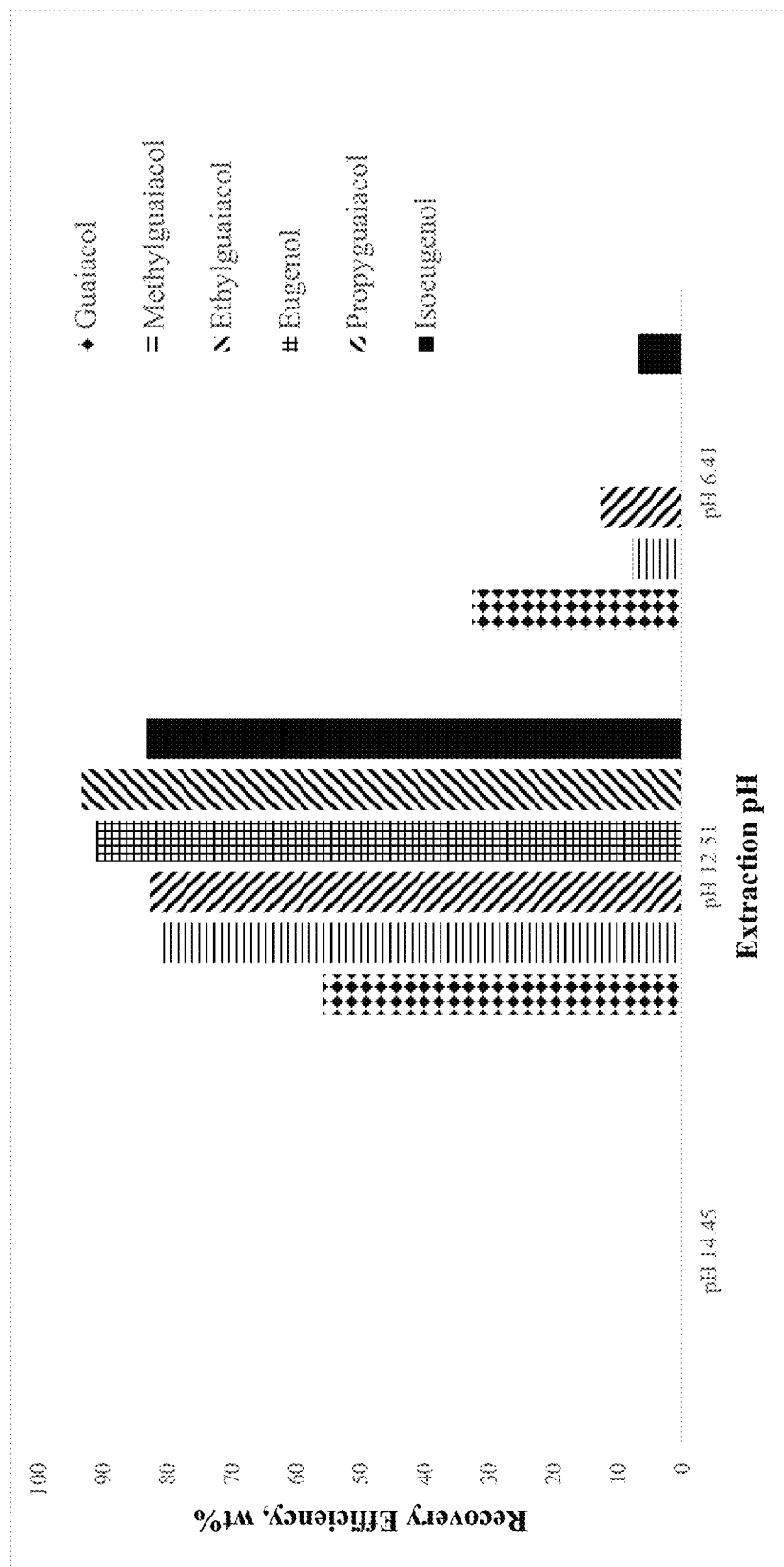
FIG. 5 is a chart showing the recovery efficiency for each methoxyphenol at each pH level in accordance with Example 1.

FIG. 5 provides a chart showing the recovery efficiency for each methoxyphenol at each pH level. As shown, over 90 wt % of eugenols and dihydroeugenol was recovered at pH of 12.51. The recovery of isoeugenol, methylguaiacol, and ethylguaiacol were each around 80 wt %, respectively. The recovery for guaiacol was the lowest (56 wt %) at the 12.51 pH level. The results confirmed the hypothesis that the methoxyphenols can be extracted at higher pH levels.

Figure 6:
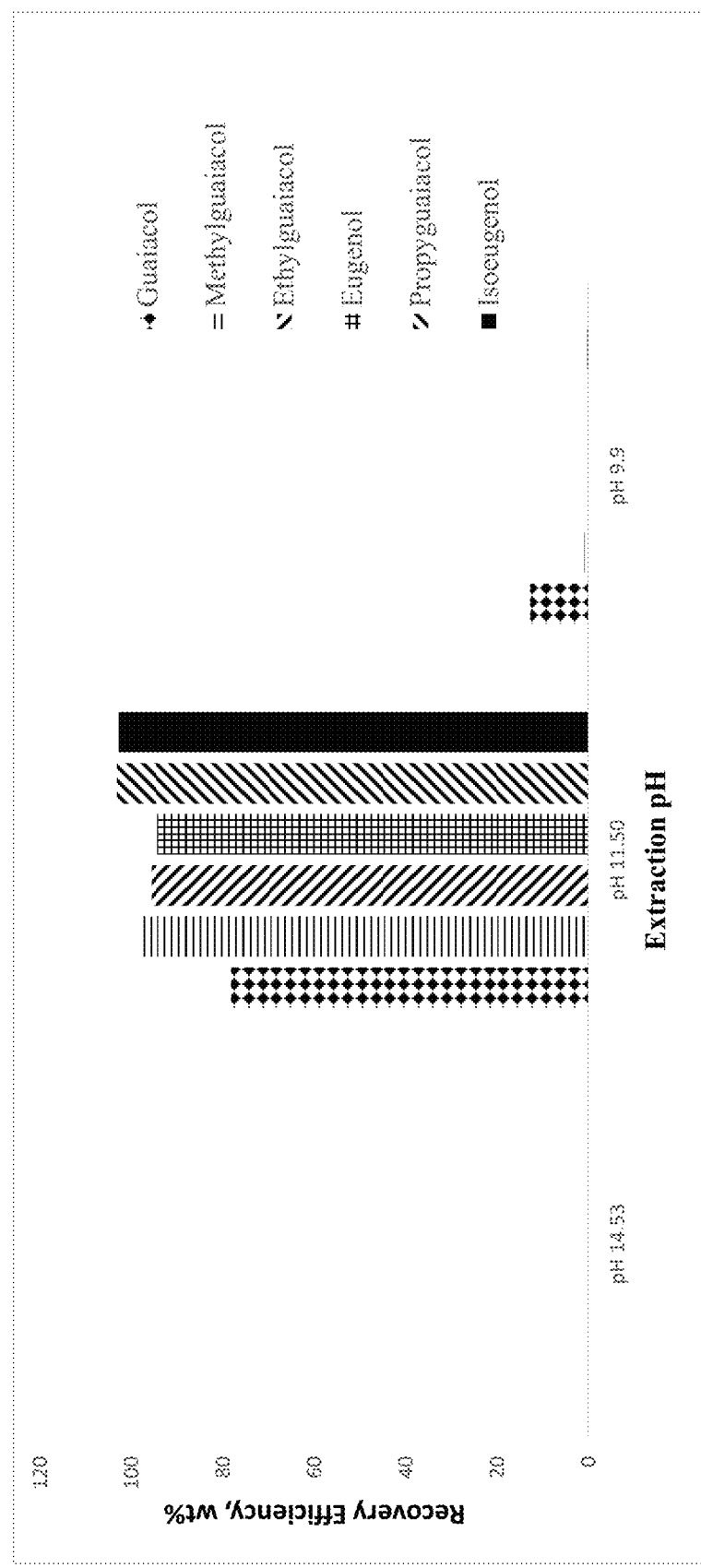
FIG. 6 is an additional chart showing the recovery efficiency for each methoxyphenol at each pH level in accordance with Example 1.
Figure 7A:
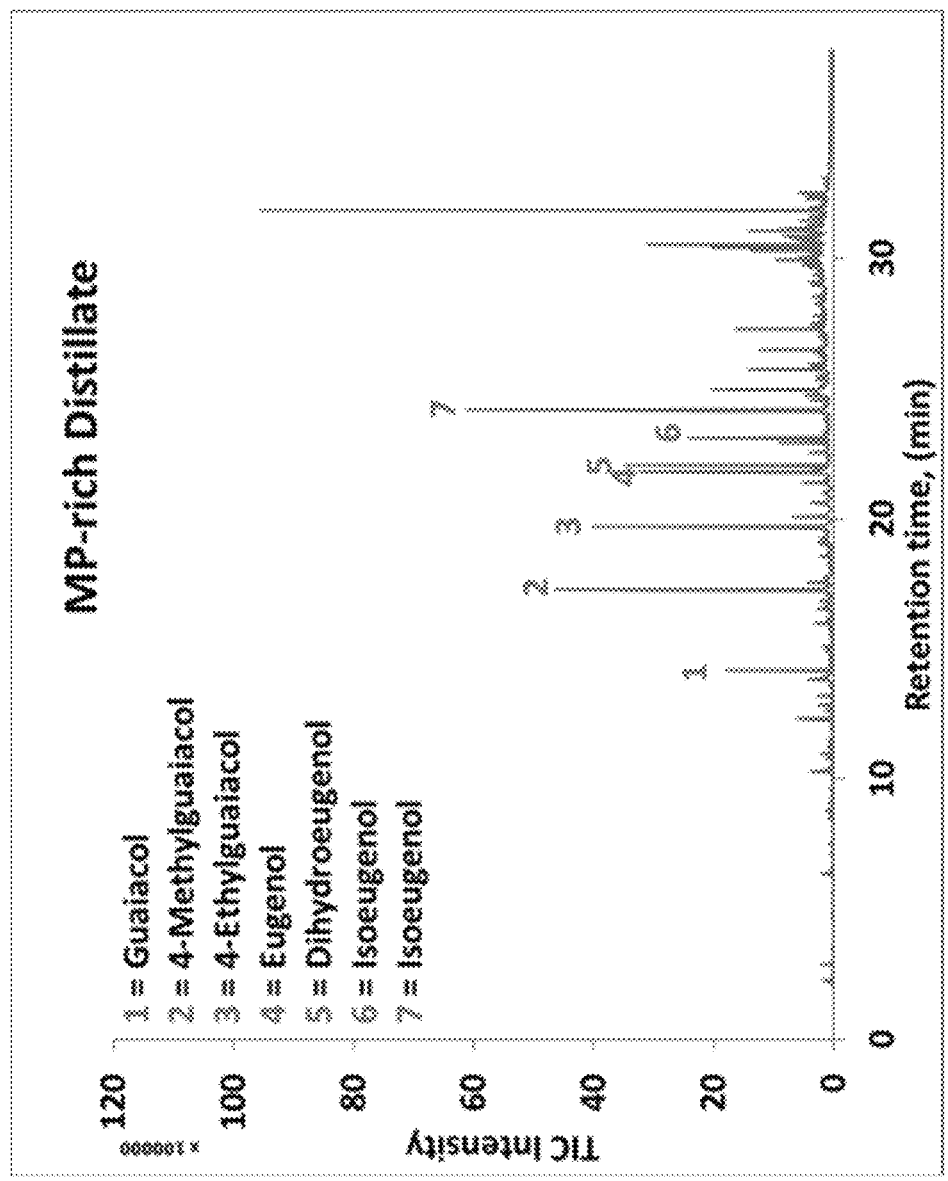
FIGS. 7A, 7B, 7C, and 7D are GC-MS chromatograms of the MP rich distillate, the extract at pH of 14.53, the extract at pH of 11.5, and the extract at pH of 10, respectively, in accordance with Example 1.
Figure 7B:
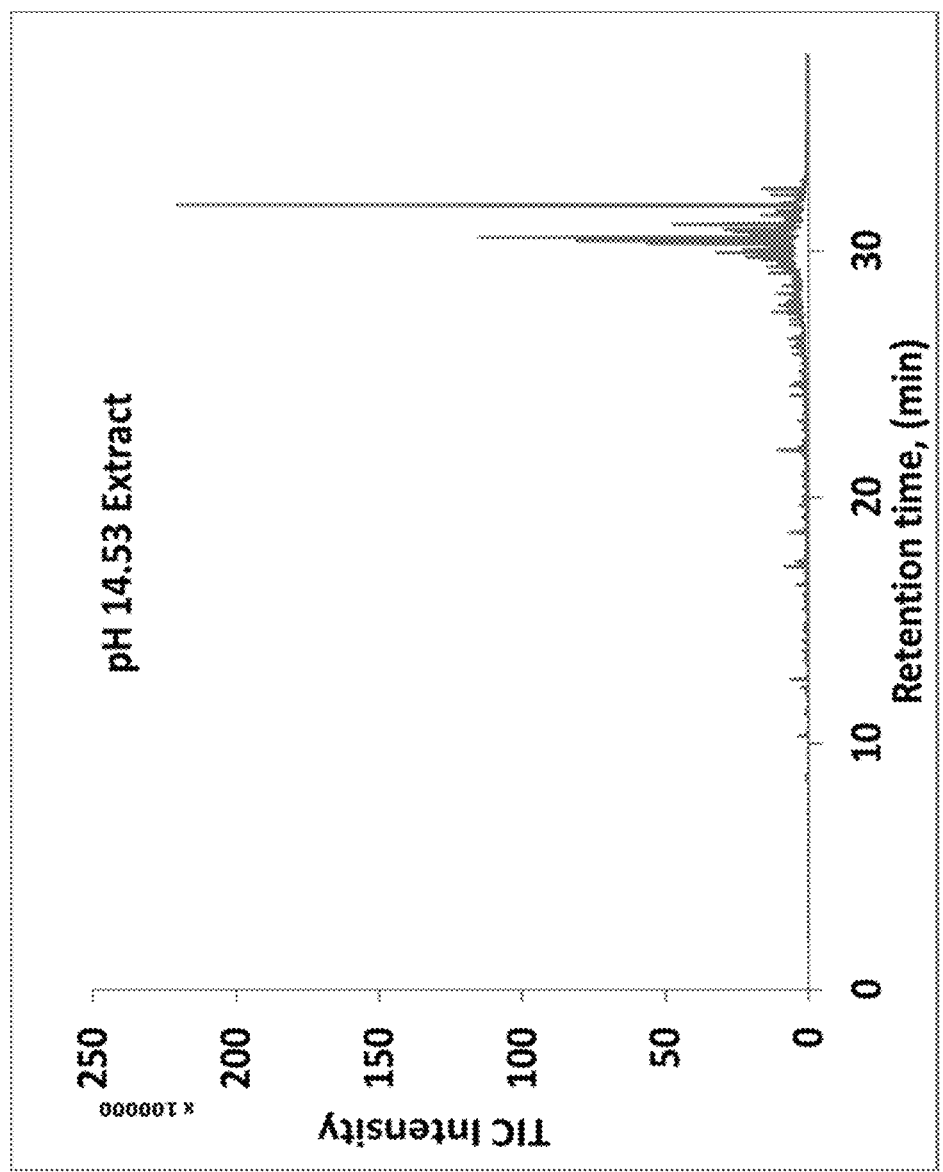
Figure 7C:
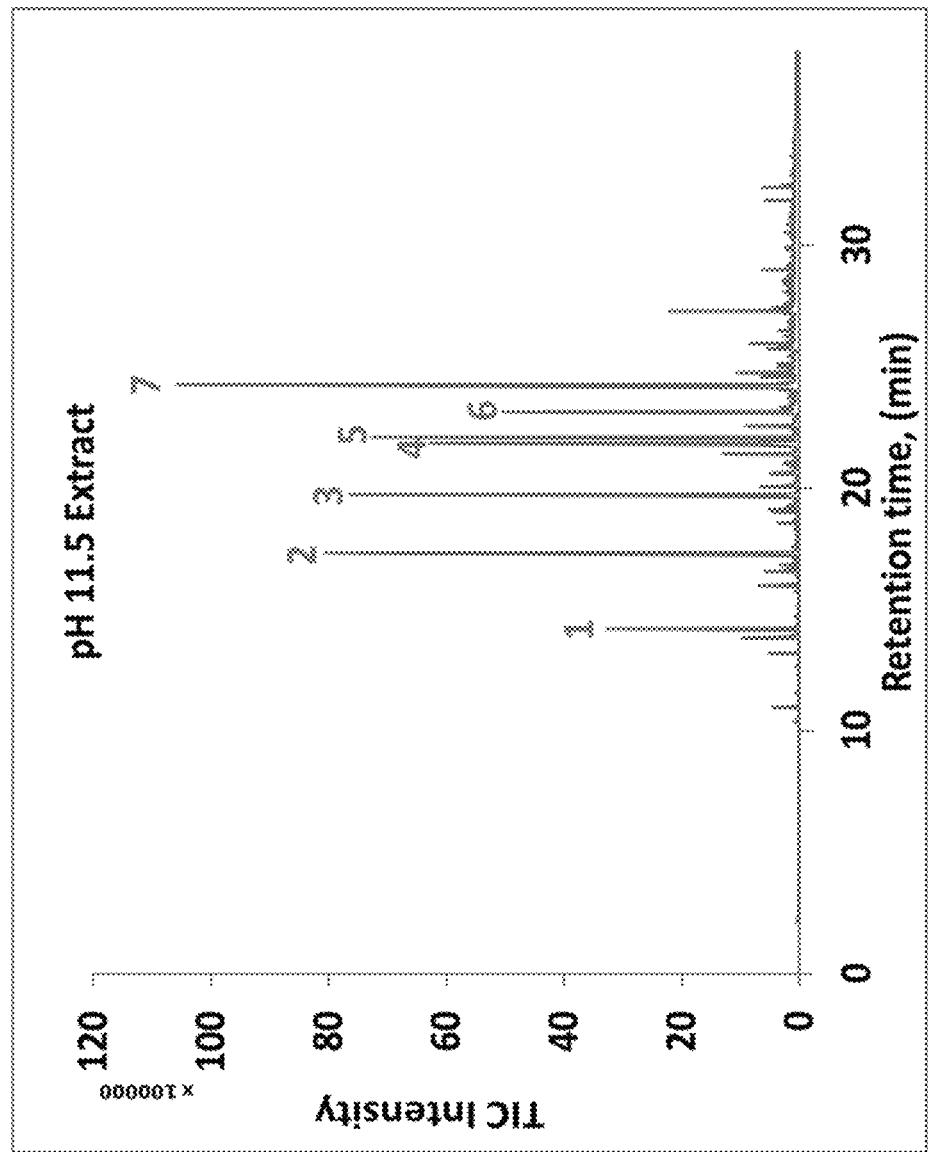
Figure 7D:
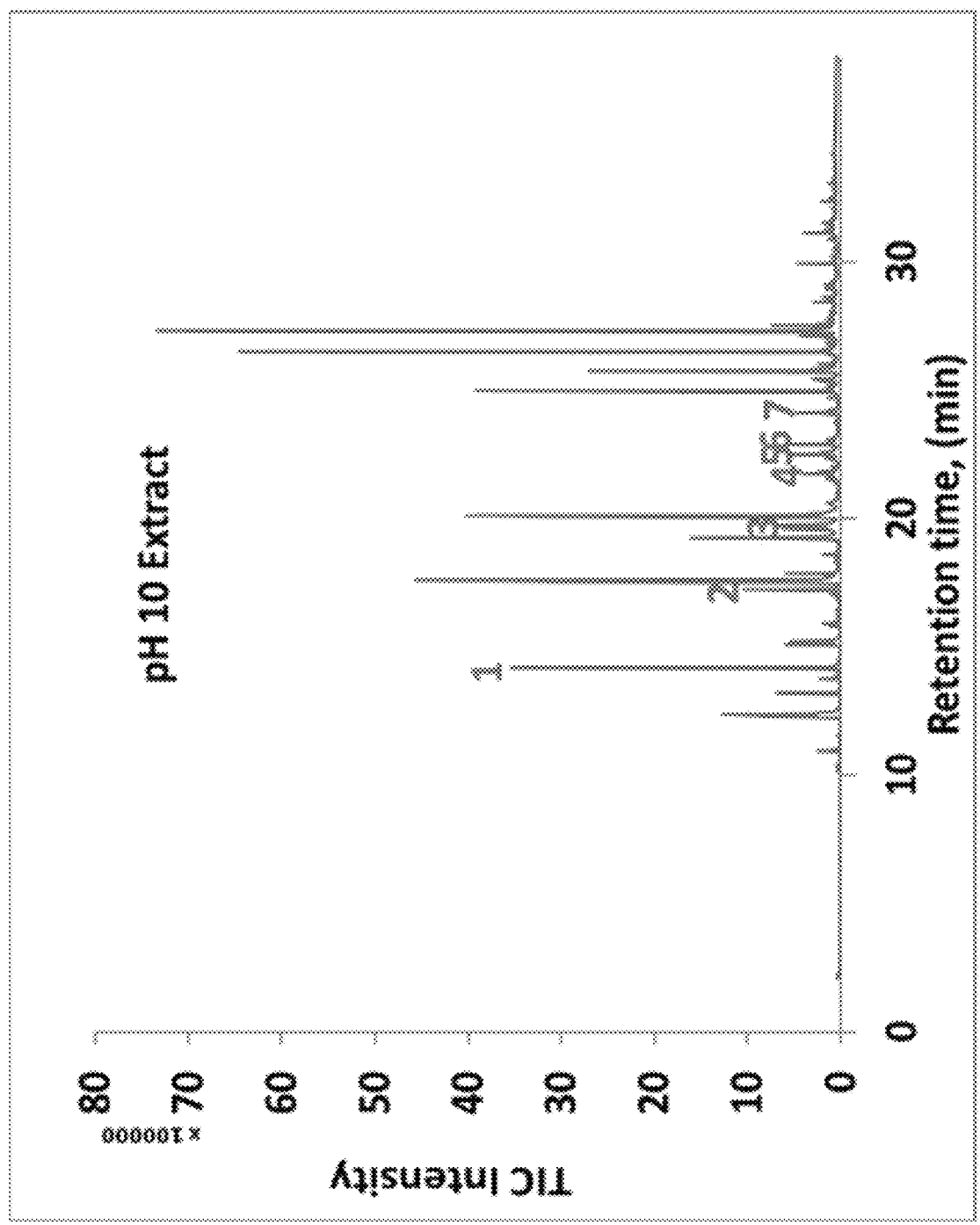

It was noticed that extraction of the MPs at a higher pH, such as 12.5, appeared to disfavor guaiacol recovery. As a result, a lower pH level (11.5) was evaluated. Following similar protocols, extractions were performed sequentially at the following pH levels: 14.53, 11.50, and 9.99. FIG. 6 provides a chart showing the recovery efficiency for each methoxyphenol at each pH level. The results show that the extraction of the MPs at pH 11.5 improved the recovery of guaiacol to about 80 wt %. Also, the results showed higher recoveries (over 94 wt %) for eugenols, dihydroeugenol, isoeugenol, methylguaiacol, and ethylguaiacol.

FIGS. 7A, 7B, 7C, and 7D are GC-MS chromatograms of the MP rich distillate, the extract at pH of 14.53, the extract at pH of 11.5, and the extract at pH of 10, respectively. The extract at pH of 11.5 contains primary monofunctional methoxyphenols and simple phenols; while the extract at pH 10 contains dominantly catechols and multifunctional phenolics like 4-hydroxy-3-methoxy-benzeneacetic acid, 1,2-dimethoxy-4-n-propylbenzene, 1-(4-hydroxy-3-methoxy-phenyl)-ethanone, 4-(2-hydroxyethyl)-2-methoxyphenol, and 4-hydroxy-3-methoxybenzaldehyde.

Additionally, three solvents with different polarity indexes; dichloromethane (DCM), methyl isobutyl ketone (MIBK), and hexane were evaluated in comparison to MTBE. Extraction of the MPs was performed at a pH of 11.5 following previously described protocols; 50 wt % NaOH solution and 6N HCl were used. Table 3 shows the recovery efficiencies obtained for each solvent. Extraction with hexane had the lowest recovery efficiency (67%), but the extract had the highest MP concentration (72.4 wt %). Unexpectedly, extraction with MIBK resulted in relatively lower recovery efficiency, and the extract also had lower concentration of MPs. The MTBE and DCM solvents provided high recovery efficiencies and moderate concentration of MPs. Because the hexane solvent gave higher concentration of MPs, it was realized that it could be used to wash extracts from alkaline extraction with MTBE or DCM as a purification step.

TABLE 3

Effect of organic solvent on recovery efficiency

| Solvent | MPs recovery efficiency, wt % | Concentration of MPs in Extract |
| --- | --- | --- |
| Hexane | 66.98 | 72.4 |
| MIBK | 81.37 | 33.8 |
| MTBE | 97.77 | 49.7 |
| DCM | 98.69 | 51.4 |

Examples of the Integrated Recovery Method

Figure 8:
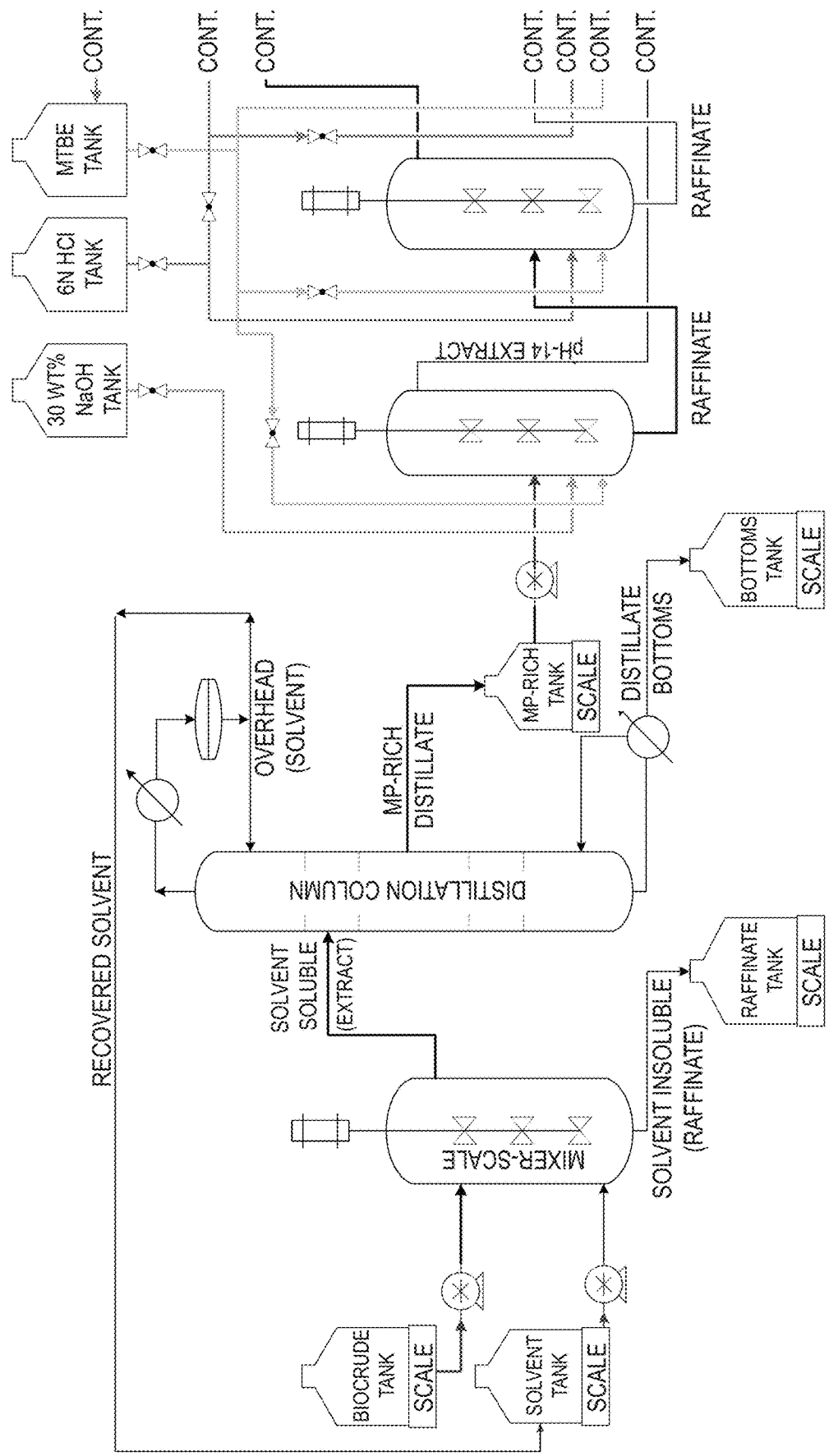
FIG. 8 is an exemplary process flow diagram illustrating an embodiment of the integrated recovery method (Strategy 1).
Figure 8:
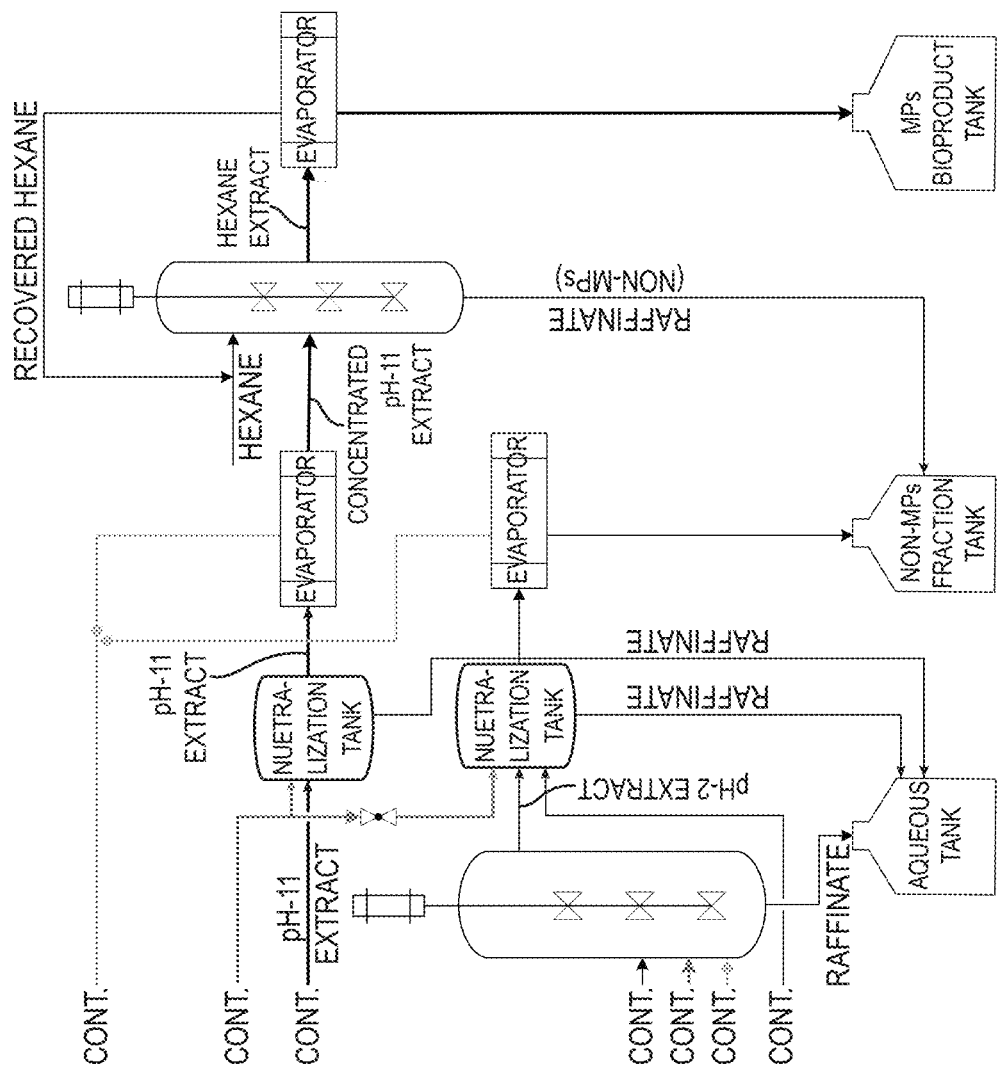
Figure 9:
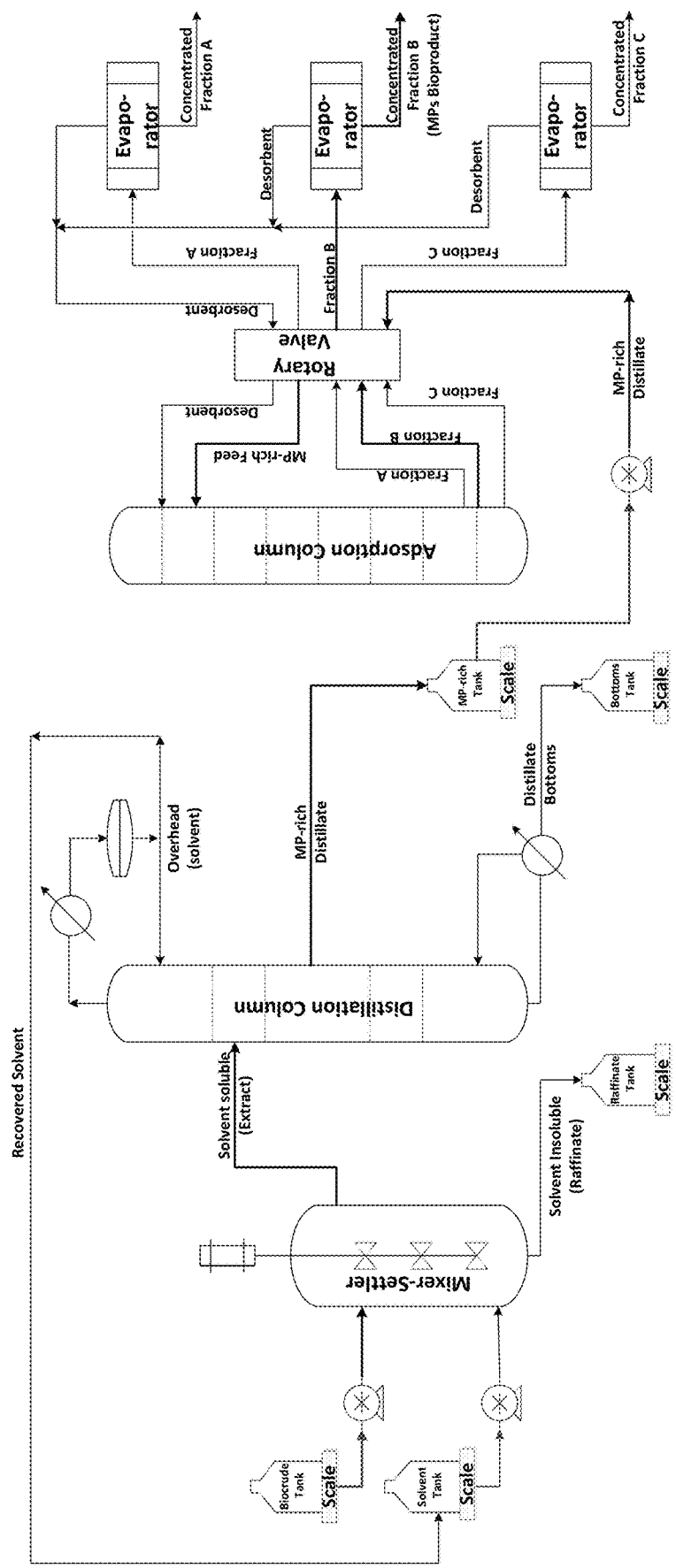
FIG. 9 is an exemplary process flow diagram illustrating an embodiment of the integrated recovery method (Strategy 2).
Figure 10:
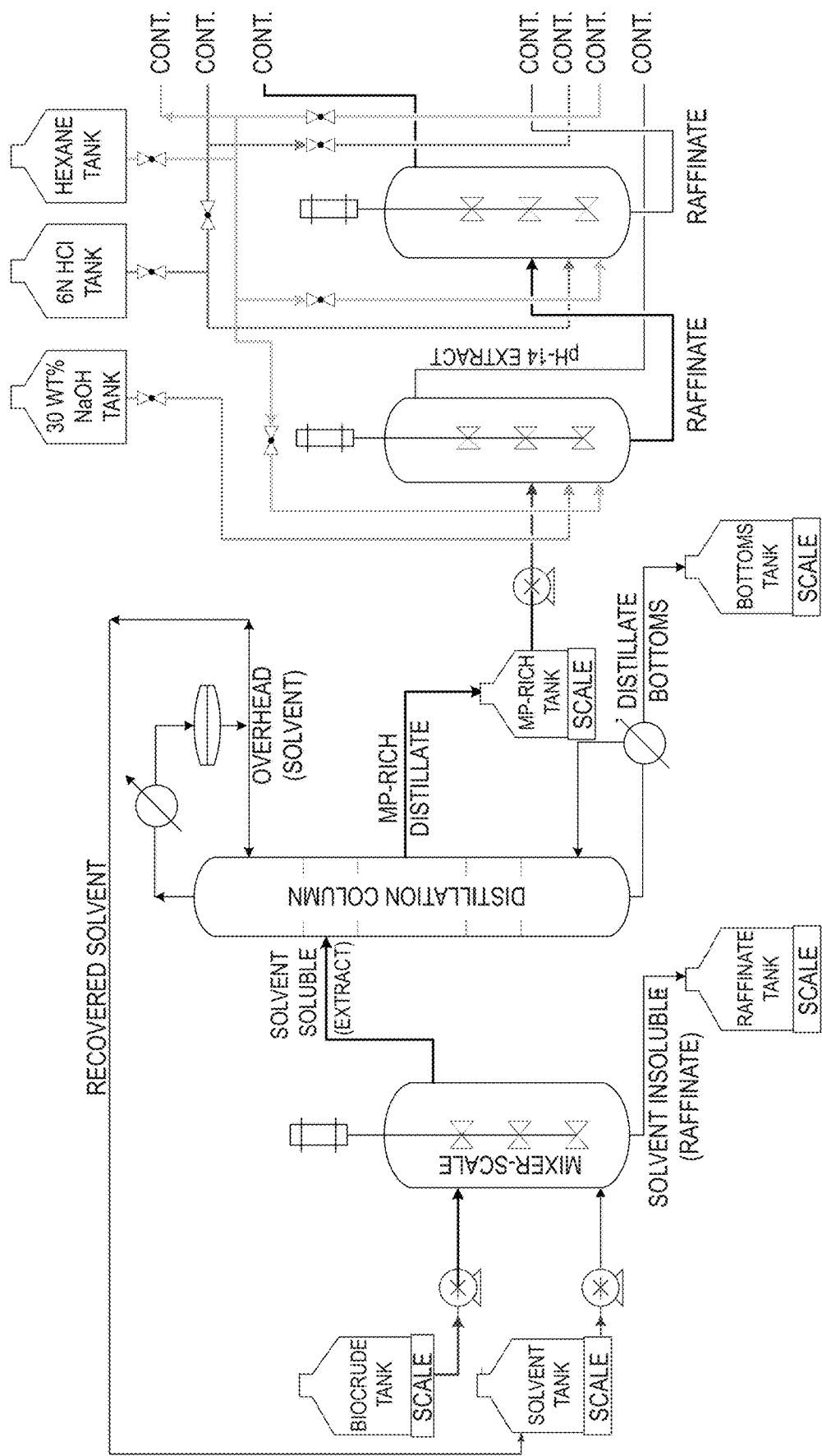
FIG. 10 is an exemplary process flow diagram illustrating an embodiment of the integrated recovery method (Strategy 3).
Figure 10:
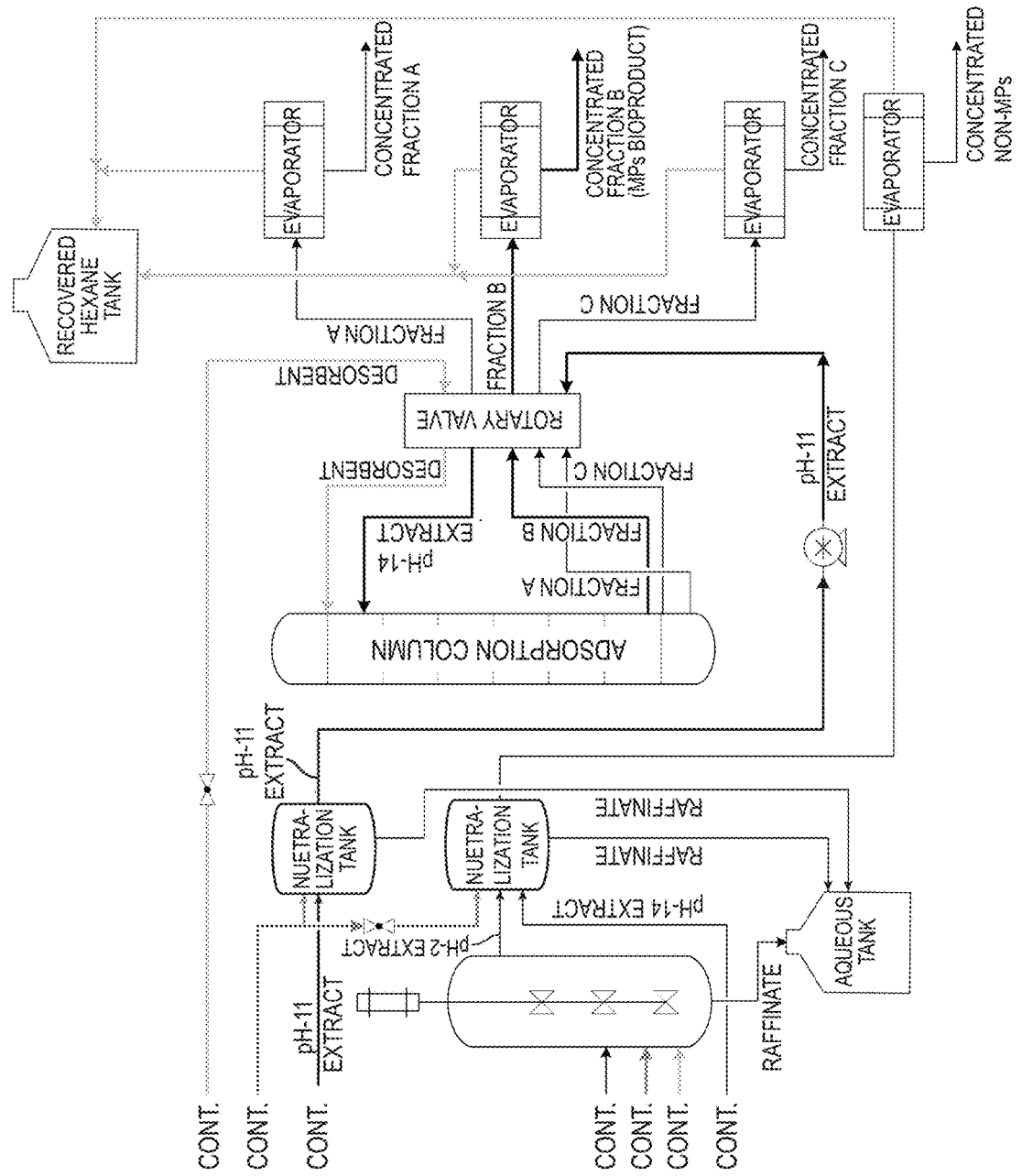

More detailed process flow diagrams for the three processing strategies discussed above (Strategy 1, Strategy 2, and Strategy 3) are provided in FIGS. 8, 9, and 10. The overall efficiency of the integrated recovery method and the purity of the MP bio-products vary with the efficiency of the individual separation techniques used within the integrated strategy. As will be seen in the examples below, the isolation step can have a recovery between about 70 wt % and 95 wt %, preferably between about 75 wt % and 95 wt %. The concentration step can have a recovery between about 70 wt % and 95 wt %, preferably between about 75 wt % and 95 wt %.

For the isolation step of the hybrid processing strategies, the lowest recovery was about 73 wt % and the highest was about 90.8 wt %. In the concentration step, the recoveries were between 77.0 wt % and 94.0 wt %. The purification step recovery efficiencies varied between 64.4 wt % and 91.3 wt %. The highest overall efficiency obtained for the integrated recovery method was 73.9 wt %. The differences observed were due to the diverse conditions explored during the development of the hybrid method.

Table 4 shows the average concentration of the targeted methoxyphenols in the biocrude used and the product streams from each separation step.

TABLE 4

Concentration of individual methoxyphenol

| | Methoxyphenol Distribution, wt % | | | |
| --- | --- | --- | --- | --- |
| Compounds | Biocrude | Isolation Step | Concentration Step | Purification Step |
| Guaiacol | 0.9 ± 0.04 | 3.3 ± 0.42 | 3.2 ± 1.12 | 3.8 ± 0.78 |
| 4-methylguaiacol | 2.3 ± 0.12 | 9.1 ± 0.80 | 14.3 ± 2.03 | 20.3 ± 1.54 |
| 4-ethylguaiacol | 1.4 ± 0.11 | 5.6 ± 0.62 | 10.1 ± 0.71 | 13.9 ± 1.84 |
| Eugenol | 1.4 ± 0.20 | 5.8 ± 1.10 | 11.3 ± 0.84 | 14.4 ± 1.89 |

TABLE 4-continued

Concentration of individual methoxyphenol

| | Methoxyphenol Distribution, wt % | | | |
|---|---|---|---|---|
| Compounds | Biocrude | Isolation Step | Concentration Step | Purification Step |
| 4-propylguaiacol | 1.0 ± 0.14 | 3.8 ± 0.56 | 7.7 ± 1.43 | 9.6 ± 1.1.90 |
| Isoeugenol (cis &Trans) | 3.8 ± 0.43 | 14.9 ± 1.44 | 25.7 ± 2.53 | 25.7 ± 8.84 |
| Total | 10.8 ± 0.98 | 42.5 ± 4.35 | 72.1 ± 6.03 | 87.8 ± 7.52 |

Hybrid Strategy 1—Distillation and Extraction

Example 2

456.5 g of biocrude with 11.6 wt % concentration of MPs was distilled in 2-stages at 20 Torr to obtain 91.6 g of a MP-rich fraction with 46.12 wt % concentration of MPs. The MP-rich fraction was then subjected to alkaline solvent extraction using 30 wt % NaOH and MTBE solvent. The recovery of the MP-rich extract was performed at pH level of 11.6 after removing the neutral components at pH level of 13.7. The MP-rich extract was then washed with hexane solvent. The final extract was about 47.6 g and the concentration of MPs was 79.18 wt %. The recovery efficiency for the distillation step was 79.7% and that for the extraction step was 89.4%. The overall recovery efficiency was 71.3%.

Example 3

In another experiment like that of example 2, 469.4 g of biocrude containing 11.6 wt % of MPs was distilled in 2-stages to obtain 94.8 g of a MP-rich fraction containing 46.52 wt % of MPs. The MP-rich fraction was then subjected to alkaline solvent extraction using 50 wt % NaOH and MTBE. The recovery of the MP-rich extract was performed at pH level of 12.51, after removing the neutral components at pH level of 14.2. The MP-rich extract was then washed with hexane solvent. The final extract was about 51.3 g and the concentration of MPs was 78.32 wt %. The recovery efficiency for the distillation step was 81.0% and that for the extraction step was 91.2%. The overall recovery efficiency was 74.0%.

Example 4

For this example, 630 g of biocrude containing 11.3 wt % of MPs was fractionated with toluene and 445 g of toluene soluble fraction (TSF) with 14.8 wt % concentration of MPs was recovered after solvent recovery. The efficiency of the fractionation step was 92.7%. In the next step, 414 g of the TSF was distilled to obtain 113.7 g of MP-rich distillate with 48.8 wt % concentration. The efficiency of the distillation step was 90.6%. Subsequently, 92.1 g of the MP-rich distillate was subjected to alkaline solvent extraction using 50 wt % NaOH and MTBE. 54.3 g of MP-rich extract with 73 wt % of MPs was recovered at pH level of 10.96 after removing the neutral components at pH level of 14.5. The extraction separation efficiency was 88.2%. The MP-rich extract was then washed with hexane to obtain a bio-product with 87.9 wt % concentration of MPs. The hexane wash efficiency was 88.4%. Overall separation efficiency was 65.4%, residual loss was negligible and the mass balance of the hybrid separation process was 98.6%.

Example 5

620 g of bio-crude containing 9.67 wt % of MPs was fractionated with toluene and 480 g of toluene soluble fraction with 10.12 wt % concentration of MPs was recovered after solvent recovery. The efficiency of the fractionation step was 81%. Subsequently, about 426.4 g of the TSF was distilled in two stages to obtain 87.13 g of MP-rich distillate with 45 wt % concentration. The efficiency of the distillation step was 90.84%. Then, 73.8 g of the MP-rich distillate was subjected to alkaline solvent extraction using 40 wt % NaOH and MTBE. 44 g of MP-rich extract with 70.3 wt % of MPs was recovered at pH level of 11.0 after removing the neutral components at pH level of 14.8. The extraction separation efficiency was 92.9%. The MP-rich extract was then washed with hexane to obtain a bioproduct with 84.7 wt % concentration of MPs. The hexane wash efficiency was 96.2%. Overall separation efficiency was 65.8%, residual loss was negligible and the mass balance of the hybrid separation process was 96.6%.

Example 6

620 g of biocrude containing 9.53 wt % of MPs was fractionated with toluene and 409.9 g of toluene soluble fraction with 12.83 wt % concentration of MPs was recovered after solvent recovery. The efficiency of the fractionation step was 89%. In the next step, about 383.6 g of the TSF was distilled to obtain 121.6 g of MP-rich distillate with 37.7 wt % concentration. The efficiency of the distillation step was 93.2%. Subsequently, 112.6 g of the MP-rich distillate was subjected to alkaline solvent extraction using 35 wt % NaOH and MTBE. 62.5 g of MP-rich extract with 57.8 wt % of MPs was recovered at pH level of 11.05 after removing the neutral components at pH level of 14.8. The extraction separation efficiency was 85.0%. The MP-rich extract was then washed with hexane to obtain a bioproduct with 73.7 wt % concentration of MPs. The hexane wash efficiency was 88%. Overall separation efficiency was 62.0%, residual loss was negligible and the mass balance of the hybrid separation process was 99.4%.

Hybrid Strategy 2-Distillation and Silica Gel Adsorption

Example 7

In this example, 615 g of biocrude with MPs concentration of 11.1 wt % was fractionated with toluene to obtain 459.7 g of toluene soluble fraction with 14.7 wt % concentration of MPs after solvent recovery. The efficiency of the fractionation step was 98.9%. In the distillation step, 406.5 g of the TSF was used and 111.1 g of MP-rich distillate with 49.3 wt % concentration was recovered. The efficiency of the distillation step was 91.7% and residual loss was zero %.

The distillate was then subjected to a silica gel adsorption; 49.3 g was used and 20.21 g of purified MPs bioproduct with 89.4 wt % concentration was obtained. The purification efficiency was 74.35 wt %. The overall efficiency was 67.4% with a mass balance of 98.9%.

Example 8

The exact experiment in example 6 was repeated for the adsorption step. 615 g of biocrude with MPs concentration of 11.1 wt % was fractionated with toluene to obtain 459.7 g of toluene soluble fraction with 14.7 wt % concentration of MPs after solvent recovery. The efficiency of the fractionation step was 98.9%. In the distillation step, 406.5 g of the TSF was used and 111.1 g of MP-rich distillate with 49.3 wt % concentration was recovered. The efficiency of the distillation step was 91.7% and residual loss was zero %. The distillate was then subjected to a silica gel adsorption; 52.1 g was used and 22.3 g of purified MPs bioproduct with 92.2 wt % concentration was obtained. The purification efficiency was 80.0%. The overall efficiency was 72.5% with a mass balance of 98.6%.

Hybrid Strategy 3-Distillation, Alkaline Extraction, and Silica Gel Adsorption

Example 9

608 g of biocrude with 10.34 wt % concentration of MPs was fractionated with toluene and 513.5 g of toluene soluble fraction was recovered after solvent recovery. The efficiency of the fractionation step was 94.08%. About 462.6 g of the TSF was distilled and 115 g of MP-rich distillate fraction was recovered. The efficiency of the distillation step was 97.96%. 104.30 g of the MP-rich distillate was then subjected to alkaline solvent extraction using 50 wt % NaOH and MTBE. 59.34 g of MP-rich extract was recovered at pH level of 11.6 after removing the neutral components at pH level of 13.7. The extraction separation efficiency was 84.6%. The MP-rich extract was then purified on a silica gel adsorption column with Hexane-DCM-methanol solvents and three fractions (A, B &C) were collected. The purity of the fractions A and B with respect to the MPs were 72.4% and 94.1% respectively. The two fractions together give a product purity of 93.1%. The final corrected recovered bioproduct was 49.9 g. The efficiency of the purification step was 94.9%. The overall separation efficiency was 73.9%. The overall mass balance of the hybrid separation process was 99.32%.

Example 10

608 g of biocrude with 10.34 wt % concentration of MPs was fractionated with toluene and 395.2 g of toluene soluble fraction was recovered after solvent recovery. The toluene insoluble fraction was 227.1 g. The efficiency of the fractionation step was 96.6%. About 364.8 g of the toluene soluble fraction was distilled and 111.5 g of MP-rich distillate fraction with MPs concentration of 49.63 wt % was recovered. The efficiency of the distillation step was 98.7%. Subsequently, 96.6 g of the MP-rich distillate was subjected to alkaline solvent extraction using 50 wt % NaOH and MTBE. 55.5 g of MP-rich extract was recovered at pH level of 11.1 after removing the neutral components at pH level of 14.23. The extraction separation efficiency was 91.5%. 51.80 g of the MP-rich extract was then purified on a silica gel adsorption column and four fractions (A, B, C, &D) were collected. The purity of the fractions A and B with respect to the MPs were 61.5% and 98.2% respectively. The two fractions together provide a bioproduct purity of 94.3%. The final corrected recovered bioproduct was 52.1 g. The efficiency of the purification step was 89.6%. The overall separation efficiency was 78.1%. The overall mass balance of the hybrid separation process was 96.18%.

Example 11

597 g of biocrude with 10.34 wt % concentration of MPs was fractionated with toluene and 486.1 g of a toluene soluble fraction was recovered after removing the solvent. The toluene insoluble fraction was 218.6 g. The fractionation process gave a toluene soluble fraction containing 12.29 wt % concentration of MP. The efficiency of the fractionation step was 96.8%. About 402.8 g of the toluene soluble fraction was distilled and 106 g of MP-rich distillate fraction with MPs concentration of 46.01 wt % was recovered. The efficiency of the distillation step was 98.5%. Subsequently, 91.3 g of the MP-rich distillate was subjected to alkaline solvent extraction using 50 wt % NaOH and MTBE. 48.30 g of MP-rich extract was recovered at pH level of 11.0 after removing the neutral components at pH level of 14.84. The alkaline extraction step gave a MP-extract with 79.3 wt % concentration of MPs and the extraction efficiency was at 91.20 wt %. 46.8 g of the MP-rich extract was then purified on a silica gel adsorption column and four fractions (A, B, C, &D) were collected. The purity of the fractions A and B with respect to the MPs were 67.3% and 99.6% respectively. The two fractions together provide a bioproduct purity of 96.8%. The final corrected recovered bioproduct was 45.6 g. The efficiency of the purification step was 82.2%. The overall separation efficiency was 71.4%. The overall mass balance of the hybrid separation process was 98.32%.

Numerous modifications and variations of the present disclosure are possible in view of the above teachings. It is understood that within the scope of the appended claims, the disclosure may be practiced otherwise than as specifically described herein.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

The invention claimed is:

1. A process for selectively recovering a phenolic compound from feedstock comprising bio-crude and/or bio-oil, wherein the recovery efficiency of the selected phenolic compound is greater than 70 wt % and the purity of the recovered selected phenolic compound is higher than 80 wt %, the process comprising:

distilling the feedstock to isolate the selected phenolic compound in a first distillate fraction comprising the selected phenolic compound, concentrating the selected phenolic compound from the first distillate fraction in a concentrated mixture, wherein concentrating comprises using sequential solvent extraction at decreasing pH levels to concentrate the selected phenolic compound in a concentrated mixture, wherein sequential solvent extraction at decreasing pH levels comprises extraction at pH levels in the following ranges: 14.5-14, 13-9.5, 8-6, and 3-0.5, and purifying the concentrated mixture to recover the selected phenolic compound.

2. The process of the claim 1, wherein an alkaline extraction solvent is used for sequential solvent extraction and the alkaline extraction solvent comprises dichloromethane, methyl isobutyl ketone, hexane or methyl tertiary butyl ether.

3. The process of claim 1, wherein purifying comprises performing adsorption on the concentrated mixture.

4. The process of claim 3, wherein adsorption comprises chromatographic separation.

5. The process of claim 3, wherein the adsorbent is silica gel.

6. The process of claim 1, wherein the selected phenolic compound comprises a methoxyphenol.

7. The process of claim 1, wherein the first distillate fraction boils at a temperature between 150° C. and 400° C.

8. The process of claim 1, wherein the selected phenolic compound comprises one or more of eugenol, dihydroeugenol, or isoeugenol.

9. A process for selectively recovering a phenolic compound from feedstock comprising bio-crude and/or bio-oil, wherein the recovery efficiency of the selected phenolic compound is greater than 70 wt % and the purity of the recovered selected phenolic compound is higher than 80 wt %, the process comprising:

fractionating the feedstock into a volatile fraction and a non-volatile fraction using a solvent then distilling the volatile fraction to isolate the selected phenolic compound in a first distillate fraction comprising the selected phenolic compound, concentrating the selected phenolic compound from the first distillate fraction in a concentrated mixture, and purifying the concentrated mixture to recover the selected phenolic compound.

10. The process of claim 9, wherein the solvent is non-toxic, has a polarity index less than 3.2, and water solubility less than 0.5 g/100 mL.

11. The process of claim 10, wherein the solvent is non-toxic, has a polarity index greater than 2 and less than 3.2, and water solubility between 0.01 and less than 0.5 g/100 mL.

12. The process of claim 9, wherein the solvent is aromatic and has a boiling point less than 185° C.

13. The process of claim 9, wherein the solvent comprises toluene, xylene, ortho-xylene, chlorobenzene, dichlorobenzene, reformate, or light cycle oil.

14. The process of claim 9, wherein fractionating comprises more than one solvent fractionation step.

15. The process of claim 9, wherein purifying comprises performing adsorption on the concentrated mixture.

16. The process of claim 15, wherein adsorption comprises chromatographic separation.

17. A process for selectively recovering a phenolic compound from feedstock comprising bio-crude and/or bio-oil, wherein the recovery efficiency of the selected phenolic compound is greater than 70 wt % and the purity of the recovered selected phenolic compound is higher than 80 wt %, the process comprising:

distilling the feedstock to isolate the selected phenolic compound in a first distillate fraction comprising the selected phenolic compound, concentrating the selected phenolic compound from the first distillate fraction in a concentrated mixture, and purifying the concentrated mixture to recover the selected phenolic compound, wherein distilling comprises co-distilling the feedstock with a liquid that can solubilize at least a portion of the feedstock wherein the liquid has a higher boiling point than a boiling range of the selected phenolic compound.

18. The process of claim 17, wherein the liquid comprises glycerol and/or triethylene glycol.

* * * * *